(12) United States Patent
Candau et al.

(10) Patent No.: US 6,818,206 B2
(45) Date of Patent: Nov. 16, 2004

(54) USE OF AMPHIPHILIC COPOLYMERS TO STABILIZE DISPERSIONS OF INSOLUBLE ORGANIC COMPOUNDS FOR SCREENING OUT UV RADIATION, DISPERSIONS STABILIZED WITH THESE COPOLYMERS AND COSMETIC COMPOSITIONS CONTAINING THEM

(75) Inventors: Didier Candau, Bievres (FR); Fabien Aubert, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/268,081

(22) Filed: Oct. 10, 2002

(65) Prior Publication Data

US 2003/0129151 A1 Jul. 10, 2003

(30) Foreign Application Priority Data

Oct. 11, 2001 (FR) ............................................. 01 13114

(51) Int. Cl.[7] .............................. A61K 7/42; A61K 7/44; A61K 7/00; C07D 249/16
(52) U.S. Cl. ........................... 424/59; 424/60; 424/400; 424/401; 548/260
(58) Field of Search ........................... 424/59, 60, 400, 424/401; 548/260

(56) References Cited

U.S. PATENT DOCUMENTS

| | | | |
|---|---|---|---|
| 5,869,030 A | 2/1999 | Dumler et al. | 424/59 |
| 5,980,872 A | 11/1999 | Luther et al. | 424/59 |
| 6,235,271 B1 | 5/2001 | Luther et al. | 424/59 |
| 6,409,998 B1 * | 6/2002 | Candau et al. | 424/59 |

FOREIGN PATENT DOCUMENTS

| | | |
|---|---|---|
| DE | 198 56 728 | 6/2000 |
| EP | 1 068 866 | 1/2001 |
| WO | WO 00/37027 | 6/2000 |
| WO | WO 00/51550 | 9/2000 |

* cited by examiner

*Primary Examiner*—Shelley A. Dodson
(74) *Attorney, Agent, or Firm*—Steptoe & Johnson LLP; D. Douglas Price

(57) ABSTRACT

The invention relates to the use of at least one amphiphilic copolymer comprising at least one hydrophilic block and at least one hydrophobic block to stabilize dispersions of insoluble organic compounds comprising at least one group that absorbs UV radiation, which is in the form of particles with a mean size of between 10 nm and 5 μm, and also to dispersions stabilized with these amphiphilic copolymers and to cosmetic compositions for topical application, in particular antisun compositions, containing them.

33 Claims, No Drawings

USE OF AMPHIPHILIC COPOLYMERS TO STABILIZE DISPERSIONS OF INSOLUBLE ORGANIC COMPOUNDS FOR SCREENING OUT UV RADIATION, DISPERSIONS STABILIZED WITH THESE COPOLYMERS AND COSMETIC COMPOSITIONS CONTAINING THEM

The present invention relates to the use of amphiphilic copolymers to stabilize dispersions of insoluble organic compounds comprising at least one group that absorbs UV radiation, which are in the form of particles with a mean size of between 10 nm and 5 μm, to the dispersions obtained, stabilized with these copolymers, and to cosmetic compositions containing them, and also to a process for preparing such dispersions.

Many cosmetic compositions for photoprotecting the skin have been proposed to date.

These antisun compositions are often in the form of an emulsion of oil-in-water or water-in-oil type, of gels or of anhydrous products containing one or more organic and/or mineral, insoluble and/or soluble, lipophilic and/or hydrophilic screening agents capable of selectively absorbing harmful UV radiation. The efficacy of these screening agents is characterized by their molar extinction coefficient ε. The nature and concentration of the screening agents in the antisun compositions are chosen as a function of the desired protection factor and the desired protection profile. Depending on their lipophilic or hydrophilic nature, the screening agents may be distributed either in the fatty phase or in the aqueous phase of the antisun composition.

A large number of organic screening agents commonly used bear substituents that make them soluble in various cosmetic media: chains of 2-ethylhexyl type, for example, make screening agents soluble in oils, and ionized groups such as sulphonic acid give them a certain level of solubility in polar solvents and in particular in water.

However, it has been observed that the presence of substituents on the chromophore results in a reduction in the absorbing power, and there is thus great interest in being able to use screening agents containing an unsubstituted chromophore in order to fully exploit their absorption properties.

However, the insolubility of these screening agents in most cosmetic solvents makes them difficult to handle. It has moreover been found that, in order to be fully effective, they must be in the form of very fine particles fully dispersed in the cosmetic medium.

One of the solutions for obtaining a satisfactory dispersion of particles of screening agents in cosmetic compositions consists in first producing a concentrated predispersion that will then be introduced into the cosmetic medium.

Such predispersions of micronized insoluble organic screening agents may be prepared by grinding up a dispersion of coarse particles in the presence of one or more suitable dispersants, to the desired particle size. These dispersants are generally compounds with interfacial activity, which position themselves at the solid/liquid interface, thus preventing the aggregation and sedimentation of the particles.

International patent application WO 97/03643 (corresponding to U.S. Pat. No. 5,980,872) and patent application EP 0 893 119 (corresponding to U.S. Pat. No. 6,235,271) describe a process for grinding (micronizing) insoluble organic screening agents in the presence of a dispersant chosen from alkylpolyglucosides of formula $C_nH_{2n+1}O(C_6H_{10}O_5)_xH$ in is which n is an integer between 8 and 16 and x is between 1.4 and 1.6.

International patent application WO 95/22959 (corresponding to U.S. Pat. No. 5,869,030) discloses a process for micronizing insoluble organic screening agents in the presence of a grinding adjuvant chosen from alkylated polyvinylpyrrolidones, copolymers of vinylpyrrolidone and of vinyl acetate, acylglutamates, copolymers of acrylic acid and of tert-octylpropenamide, ditolylethersulphonic acid/formaldehyde condensation products, Carbomer® products, a commercial mixture of fatty acid esters comprising an ethoxylated tristyrylphenol and phospholipids.

The use of the above dispersants and grinding adjuvants to stabilize dispersions of micronized organic UV screening agents nevertheless poses a certain number of problems. Specifically, although these dispersants can produce stable concentrated predispersions, the dilution of the predispersions in the cosmetic medium during the preparation of the antisun compositions is generally accompanied by an at least partial desorption of the dispersants and a destabilization of the final antisun cosmetic composition.

Attempts have been made to overcome this instability observed at the time of dilution of the predispersions by increasing the concentration of dispersants. However, it has been found that such an increase in the concentration had the consequence of harming the persistence of the insoluble organic screening agents on the skin or the hair, i.e. of promoting their removal on contact with water.

Consequently, the aim of the present invention is to find dispersants for stabilizing—at relatively low concentrations that do not harm the remanence of the screening agents—both concentrated dispersions of micronized insoluble organic screening agents and the cosmetic compositions obtained by diluting these concentrated dispersions in a cosmetic medium.

The inventors have found that one particular group of polymers having the common characteristic of comprising at least one block of hydrophilic monomers and at least one block of hydrophobic monomers, known as "amphiphilic copolymers", makes it possible to satisfactorily stabilize concentrated dispersions and dilute dispersions of fine particles of insoluble organic compounds that absorb UV radiation.

Consequently, one subject of the present invention is the use of at least one amphiphilic copolymer comprising at least one hydrophilic block and at least one hydrophobic block, to stabilize dispersions of insoluble organic compounds comprising at least one group that absorbs UV radiation, which is in the form of particles with a mean size of between 10 nm and 5 μm.

A subject of the invention is also a process for preparing such dispersions, which consists in subjecting particles of the said organic compound, suspended in a liquid medium, to a step of particle size reduction, until a mean particle size of between 10 nm and 5 μm is obtained, and in adding, before, during or after the step of particle size reduction, at least one amphiphilic copolymer comprising at least one hydrophilic block and at least one hydrophobic block.

A subject of the invention is also dispersions comprising, in a liquid medium, at least one insoluble organic compound comprising at least one group that absorbs UV radiation, in the form of particles with a mean size of between 10 nm and 5 μm, and at least one dispersant chosen from a particular group of amphiphilic copolymers comprising at least one hydrophilic block and at least one hydrophobic block, and also cosmetic compositions for topical application, in particular compositions for photoprotecting the skin and/or the hair, prepared by diluting its dispersions in a cosmetically acceptable medium.

In contrast with the dispersions of micronized organic UV screening agents, stabilized with the dispersants of the prior art (see WO 97/03643 and WO 95/22959), the dispersions of the present invention stabilized with the amphiphilic polymers described in greater detail hereinbelow remain entirely stable—i.e. no aggregation, flocculation or sedimentation of the particles is observed—when cosmetic compositions are prepared from these dispersions by dilution in a cosmetically acceptable medium. The stabilizing effect, observed at the time of dilution, is obtained for small amounts of dispersing polymers, i.e. of the order of a few milligrams per square metre of surface area of particles only, which not only reduces the costs of the starting materials for the compositions, but above all has the advantage of not impairing the remanence of the insoluble UV screening agents on the skin and/or the hair.

The photoprotective cosmetic compositions containing particles of insoluble organic UV screening agents, stabilized with the amphiphilic polymers described below, are moreover distinguished by an excellent photoprotective power and satisfactory cosmetic properties.

In the present invention, the expression "amphiphilic copolymer comprising at least one hydrophilic block and at least one hydrophobic block" means polymers comprising at least two types of monomer "block", each of the blocks consisting of a succession of identical monomers. The amphiphilic polymers of the present invention may have a linear structure in which the various blocks are linked together, alternately (hydrophilic/hydrophobic), one after the other. This type of polymer including diblock, triblock or polyblock linear structures is generally known in the field of macromolecular chemistry as "block copolymers". However, the investors also intend to include in the definition of the amphiphilic copolymers used in the present invention polymers having a branched structure, for example a structure in which blocks of a first type (hydrophobic or hydrophilic) are attached to a main chain forming a second type of block (hydrophilic or hydrophobic). These polymers are generally known as "grafting copolymers" or "copolymers with a comb structure".

All these copolymers are known in the art and may be prepared according to processes such as free-radical polymerization followed by a step of polymerization-grafting, anionic or cationic polymerization, polycondensation, or alternatively according to a recent technique known as "controlled free-radical polymerization" described, inter alia, in "New Method of Polymer Synthesis", Blackie Academic & Professional, London, 1995, volume 2, page 1, or in Trends Polym. Sci. 4, page 183 (1996) by C. J. Hawker, and especially by atom-transfer free-radical polymerization described in JACS, 117, page 5614 (1995), by Matyjasezwski et al.

The amphiphilic copolymers comprising at least one hydrophilic block and at least one hydrophobic block, used for the stabilization of dispersions of particles of insoluble UV screening agents in a liquid medium, are preferably nonionic polymers. Specifically, given that the predispersions and the cosmetic compositions prepared therefrom generally contain an aqueous phase, the presence of many charges on the dispersing polymer would excessively increase its solubility in the dispersing medium and would consequently promote the desorption at the time of dilution with a cosmetically acceptable medium.

Examples of preferred amphiphilic copolymers that may be mentioned as dispersants in the present invention include:

(1) polyalkoxylated aliphatic alcohols of formula:

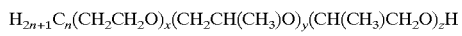

in which n is an integer between 5 and 20 and preferably between 7 and 19, x is an integer between 2 and 20 and preferably between 4 and 10, y is an integer between 2 and 20 and preferably between 4 and 10, the sum of y+z being an integer between 2 and 20 and preferably between 2 and 12.

These products are marketed under the name Synperonic®, series LF and A, and the name Atplus® by Uniquema.

(2) triblock copolymers of ethylene oxide and of propylene oxide, of formula

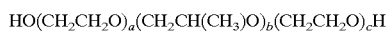

in which a represents an integer between 2 and 150, b represents an integer between 10 and 80 and c represents an integer between 2 and 150; the hydrophilic/lipophilic balance of these polymers varies as a function of the values of a, b and c.

(3) products of condensation of block copolymers of ethylene oxide and of propylene oxide with ethylenediamine, corresponding to the formula:

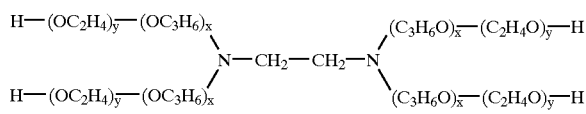

these products being marketed by Uniquema, (4) block copolymers of styrene and of ethylene oxide. This type of polymer is marketed, for example, under the name Tegomer® by Goldschmidt.

(5) polyalkoxylated fatty alcohol diurethane polymers of formula:

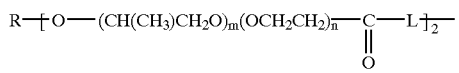

in which n represents a number between 40 and 70, m represents a number between 5 and 20, R represents a $C_{8-30}$ alkyl group and L represents a group derived from isophorone diisocyanate or from hexamethylene diisocyanate. Examples of these products that may be mentioned include PPG-14 laureth-60 isophoryldicarbamate (INCI name) and PPG-14 palmeth-60 hexyldicarbamate (INCI name), which are sold, respectively, under the names Elfacos® T211 and Elfacos® T212 by Akzo.

(6) polyethoxylated polyolefin succinates, and in particular the polyethoxylated polyisobutylene succinate of formula

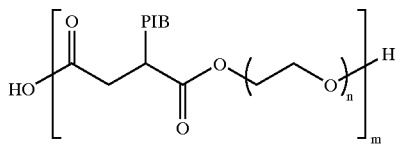

in which

PIB represents a polyisobutylene chain, n represents an integer between 2 and 15 and preferably between 7 and 10, and m represents an integer between 2 and 15 and preferably between 2 and 6.

These polymers may be prepared by condensation of a polyolefin such as polyisobutylene with succinic anhydride according to the reaction:

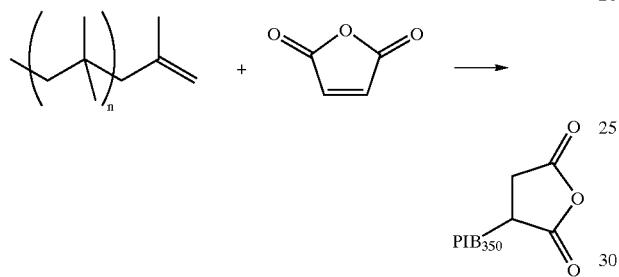

followed by a polyethoxylation of the polyolefin succinate obtained. This type of product is sold, for example, under the name OS149480 by Lubrizol.

(7) block terpolymers of (meth)acrylic acid, of a $C_{10-30}$ alkyl (meth)acrylate and of polyethylene glycol (meth) acrylate.

Preferred polymers of this family that may be mentioned include terpolymers of acrylic acid, of a $C_{15}$ alkyl acrylate and of polyethylene glycol acrylate (28 EO), sold, for example, under the name Dapral® GE 202 by Akzo.

The insoluble organic compounds comprising at least one group that absorbs UV radiation, used in the present invention, are known.

For the purposes of the present invention, the expression "insoluble organic compound" means an organic compound that has a solubility in water of less than 0.1% by weight and a solubility of less than 1% by weight in most organic solvents, for instance liquid paraffin, fatty alkylbenzoates and fatty acid triglycerides.

The insoluble organic compounds comprising at least one group that absorbs UV radiation may be chosen especially from insoluble organic UV screening agents of oxalanilide, triazine, benzotriazole, vinylamide, cinnamide, benzazole, benzofuran, arylvinylidene ketone, acrylonitrile amide, acrylonitrile sulphonamide, acrylonitrile carbamate and phenylenebis-(benzoxazinone) type.

Among the insoluble UV screening agents of oxalanilide type that may be mentioned are those corresponding to the formula:

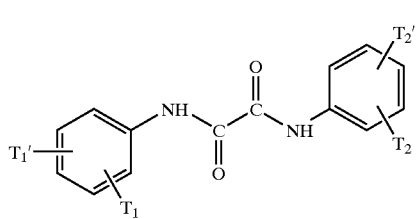

in which $T_1$, $T_1'$, $T_2$ and $T_2'$ each independently represent a $C_1$–$C_8$ alkyl radical or a $C_1$–$C_8$ alkoxy radical.

These compounds are described in patent application WO 95/22959. Examples that may be mentioned include the commercial products Tinuvin® 315 and Tinuvin® 312 sold by Ciba-Geigy and corresponding, respectively, to the formula:

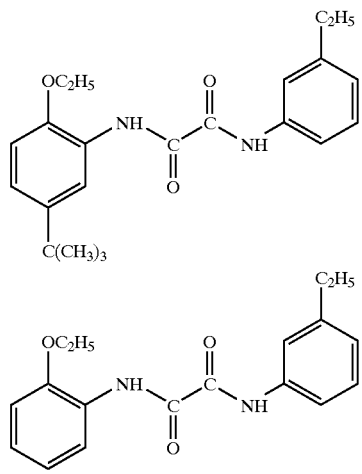

The insoluble screening agents of triazine type correspond to the following general formula:

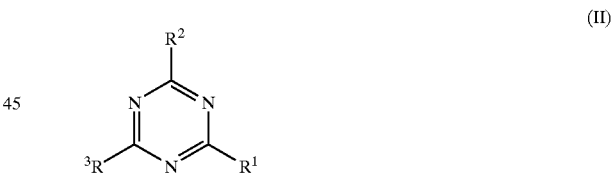

in which $R_1$, $R_2$ and $R_3$ each independently represent a phenyl, phenoxy or pyrrolo group that is unsubstituted, or each independently bear one, two or three substituents chosen from —OH, $C_{1-18}$ alkyl, $C_{1-18}$ alkoxy, carboxy($C_{1-18}$ alkyl), $C_5$–$C_8$ cycloalkyl, methylbenzylidenecamphor, —(CH=CR')$_n$(CO)—OR$_4$ in which R' represents a hydrogen atom, a cyano group or a group COOR$_4$, with $R_4$=$C_{1-18}$ alkyl or cinnamyl, and n is 0 or 1.

These compounds are described in WO 97/03643, GB 2 286 774, EP 743 309, WO 98/22447, GB 2 319 523 and EP-A-0 790 243.

Mention will be made more particularly of the following compounds:
  2,4,6-tris(diethyl 4'-aminobenzalmalonate)-s-triazine,
  2,4,6-tris(diisopropyl 4'-aminobenzalmalonate)-s-triazine,
  2,4,6-tris(dimethyl 4'-aminobenzalmalonate)-s-triazine, and 2,4,6-tris(ethyl α-cyano-4-aminocinnamate)-s-triazine.

Among the UV screening agents of triazine type that may be used for the present invention, mention may also be made of insoluble s-triazine derivatives bearing benzotriazole and/or benzothiazole groups, such as those described in patent application WO 98/25922.

Among these compounds, mention may be made more particularly of 2,4,6-tris[(3'-benzotriazol-2-yl-2'-hydroxy-5'-methyl)phenylamino]-s-triazine and 2, 4, 6-tris[(3'-benzotriazol-2-yl-2'-hydroxy-5'-tert-octyl)-phenylamino]-s-triazine.

Among the insoluble organic UV screening agents of benzotriazole type that may be mentioned are those of formula (III) below, described, for example, in International patent application WO 95/22959:

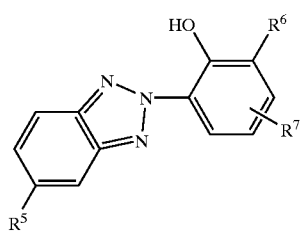

(III)

in which $R_5$ denotes a hydrogen atom or a $C_{1-18}$ alkyl radical, $R_6$ and $R_7$, which may be identical or different, each independently denote a $C_{1-18}$ alkyl radical optionally substituted with a phenyl group.

Examples of compounds of formula (III) that may be mentioned include the commercial products Tinuvin® 328, 320, 234 and 350 from Ciba-Geigy, corresponding respectively to the following formula:

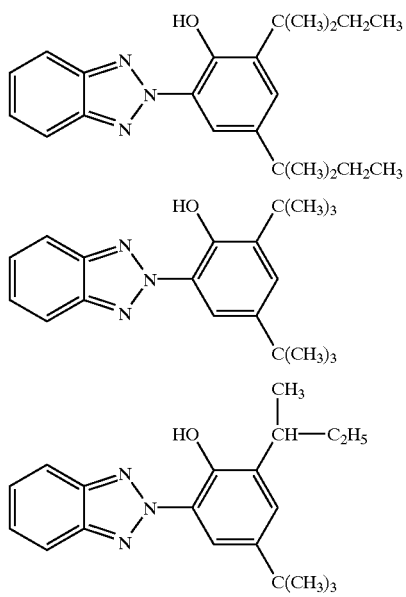

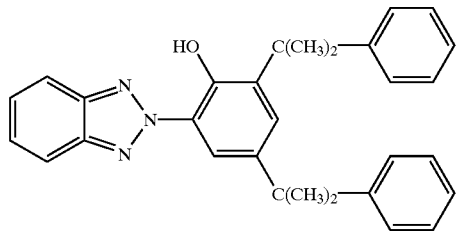

Among the insoluble organic UV screening agents of benzotriazole type that may also be mentioned are the compounds described in U.S. Pat. Nos. 5,687,521, 5,373,037 and 5,362,881, and in particular among those [2,4'-dihydroxy-3-(2H-benzotriazol-2-yl)-5-(1,1,3,3-tetramethylbutyl)-2'-n-octoxy-5'-benzoyl]diphenylmethane of formula:

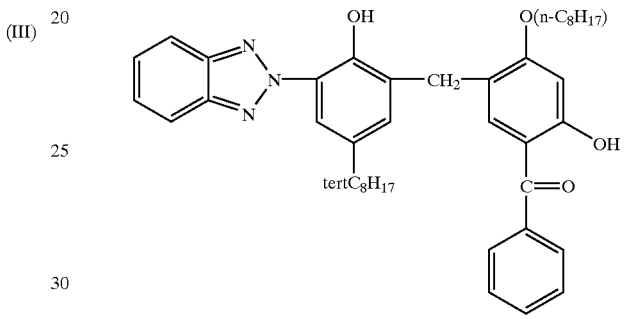

sold under the name Mixxim® PB30 by Fairmount Chemical.

Other insoluble organic UV screening agents of benzotriazole type are the methylenebis(hydroxyphenyl-benzotriazole) derivatives of the following structure:

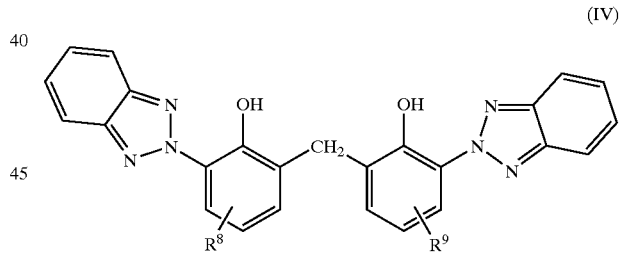

(IV)

in which $R_8$ and $R_9$, which may be identical or different, each represent a $C_{1-18}$ alkyl radical that may be substituted with one or more radicals chosen from $C_{1-4}$ alkyl, $C_{5-12}$ cycloalkyl or aryl. These compounds are known and are described in U.S. Pat. Nos. 5,237,071, and 5,166,355, and patent applications GB-A-2 303 549, DE 197 26 184 and EP-A-893 119.

In formula (IV) defined above, the $C_{1-18}$ alkyl groups may be linear or branched and are, for example, methyl, ethyl, n-propyl, isopropyl, n-butyl, isobutyl, tert-butyl, tert-octyl, n-amyl, n-hexyl, n-heptyl, n-octyl, isooctyl, n-nonyl, n-decyl, n-undecyl, n-dodecyl, tetradecyl, hexadecyl or octadecyl; the $C_{5-12}$ cycloalkyl groups are, for example, cyclopentyl, cyclohexyl or cyclooctyl; the aryl groups are, for example, phenyl or benzyl.

Among the compounds of formula (IV) that are more particularly preferred are those corresponding to the formula:

compound (a)

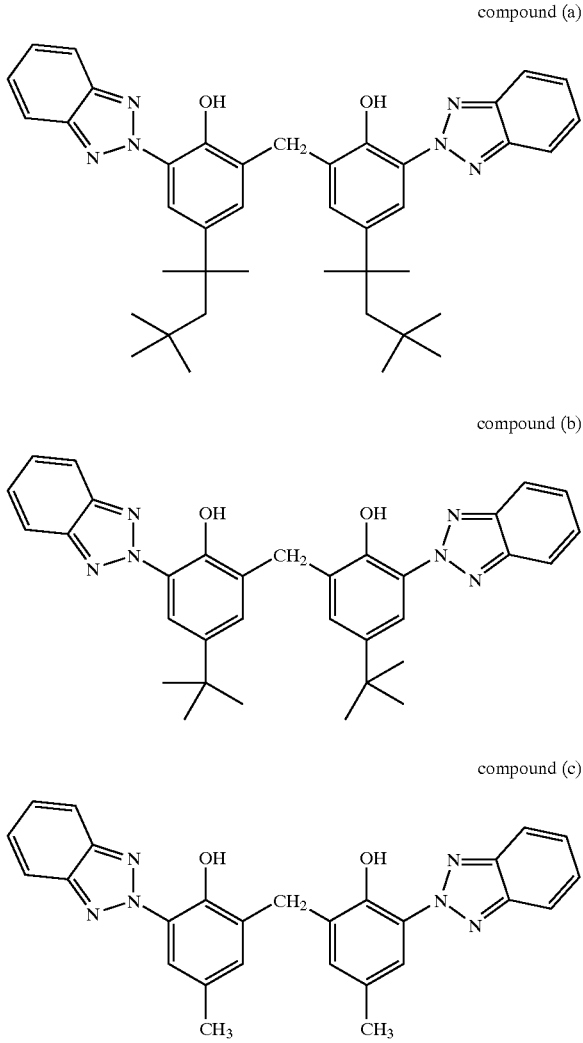

compound (b)

compound (c)

Compound (a) 2,2'-methylenebis[6-(2H-benzotriazol-2-yl)-4-(1,1,3,3-tetramethylbutyl)phenol)] is sold in pure form under the name Mixxim® BB/100 by Fairmount Chemical and in micronized form under the name Tinosorb® M by Ciba Geigy.

Compound (c) 2,2'-methylenebis[6-(2H-benzotriazol-2-yl)-4-(methyl)phenol)] is sold under the name Mixxim® BB/200 by Fairmount Chemical.

Among the insoluble organic screening agents of the vinylamide type that may be mentioned, for example, are the compounds of formula (V) that are described in patent application WO 95/22959:

$$T_3\text{—}(Y)_r\text{—}C(\!=\!O)\text{—}C(T_4)\!=\!C(T_5)\text{—}N(T_6)(T_7) \qquad (V)$$

in which $T_3$ is a $C_{1-18}$ and preferably $C_{1-5}$ alkyl radical, or a phenyl group optionally substituted with one, two or three radicals chosen from OH, $C_{1-18}$ alkyl, $C_{1-8}$ alkoxy or —C(=O)—$OT_8$ in which $T_8$ represents a $C_{1-18}$ alkyl group; $T_4$, $T_5$, $T_6$ and $T_7$ each independently represent a $C_{1-18}$ and preferably $C_{1-5}$ alkyl radical or a hydrogen atom; Y represents an —NH— group or an oxygen atom and r is 0 or 1.

Among these compounds that will be mentioned more particularly are:

4-octylamino-3-penten-2-one;

ethyl 3-octylamino-2-butenoate;

3-octylamino-1-phenyl-2-buten-1-one; and 3-dodecylamino-1-phenyl-2-buten-1-one.

Among the organic screening agents of cinnamide type that may be mentioned are compounds such as those described in patent application WO 95/22959 and corresponding to the following formula:

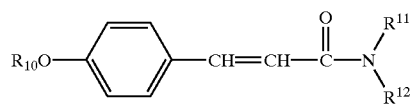 (VI)

in which $R_{10}$ represents a hydrogen atom or a $C_{1-4}$ alkyl group, preferably methyl or ethyl, $R_{11}$ represents a hydrogen atom or a $C_{1-4}$ alkyl group, preferably methyl or ethyl, $R_{12}$ represents a group —(CONH)$_s$-phenyl in which s is 0 or 1 and the phenyl group may be substituted with one, two or three groups chosen from OH, $C_{1-18}$ alkyl, $C_{1-8}$ alkoxy or —C(=O)—$OR_{13}$ in which $R_{13}$ is a $C_{1-18}$ alkyl, and more preferably $R_{12}$ represents a phenyl, 4-methoxyphenyl or phenylaminocarbonyl group.

Mention may also be made of the bis[α,β-disubstituted cinnamide] dimers described, for example, in U.S. Pat No. 5,888,481, of structure:

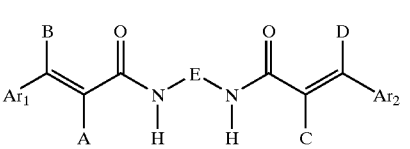 (VII)

in which $Ar_1$ and $Ar_2$, which may be identical or different, each represent a phenyl radical, an aromatic heterocycle, a group containing a fused phenyl nucleus or a group containing a fused aromatic heterocycle, and may bear one or more identical or different substituents, B and D, which are other than a hydrogen atom, each independently represent an organic radical, A and C each independently represent an organic radical, and E represents a divalent organic radical, with the exclusion of the compounds for which $Ar_1$ and $Ar_2$ both represent a phenyl group bearing a substituent —OR in which R represents a hydrogen atom or an organic radical, A and C both represent a cyano group, B and D both represent a $C_{1-35}$ alkyl or alkenyl group, and E represents a divalent organic radical, and in particular the compound of structure:

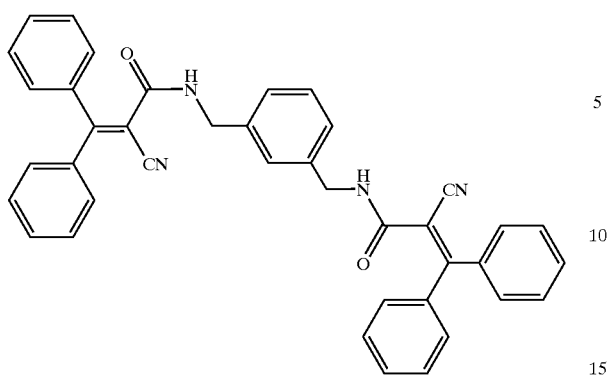

Among the insoluble organic screening agents of the benzazole type that may be mentioned are those corresponding to one of the following formula:

(VIII)

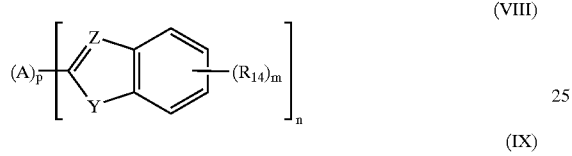

(IX)

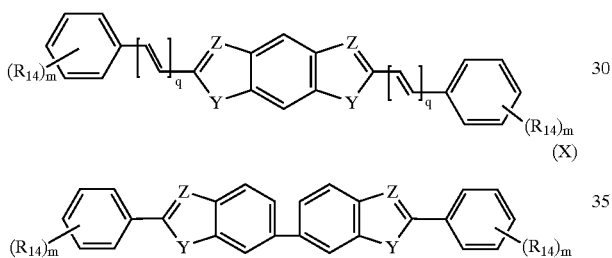

(X)

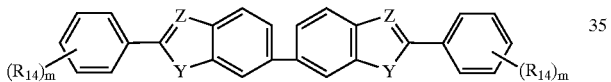

in which
- each of the symbols Y independently represents an oxygen or sulphur atom or a group $NR_{15}$,
- each of the symbols Z independently represents a nitrogen atom or a CH group,
- each of the symbols $R_{14}$ independently represents an OH group, a halogen atom, a linear or branched $C_{1-8}$ alkyl group optionally containing a silicon atom, or a linear or branched $C_{1-8}$ alkoxy group,
- each of the numbers m is independently 0, 1 or 2,
- n represents an integer between 1 and 4 inclusive,
- p is equal to 0 or 1,
- each of the numbers q is independently equal to 0 or 1,
- each of the symbols $R_{15}$ independently represents a hydrogen atom, a benzyl group or a linear or branched $C_{1-8}$ alkyl group optionally containing a silicon atom,
- A represents a radical of valency n chosen from those of formula:

(a)

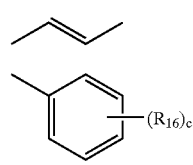

(b)

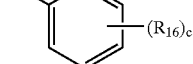

(c)

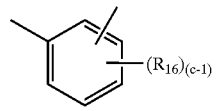

(d)

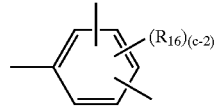

(e)

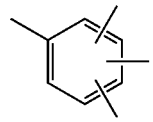

(f)

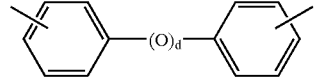

(g)

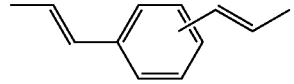

(h)

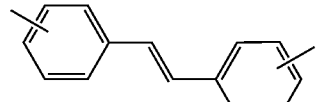

(i)

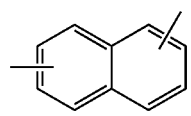

(j)

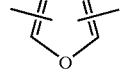

(k)

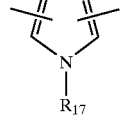

(l)

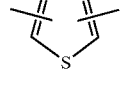

(m)

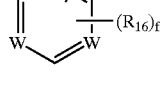

(n)

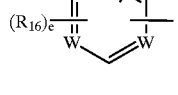

(o)

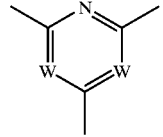

in which each of the symbols $R_{16}$ independently represents a halogen atom or a linear or branched $C_{1-4}$ alkyl or alkoxy group, or hydroxyl, $R_{17}$ represents a hydrogen atom or a linear or branched $C_{1-4}$ alkyl group, c=0–4, d=0–3, e=0 or 1 and f=0–2.

These compounds are especially described in patents DE 676 103 and CH 350 763, U.S. Pat. Nos. 5,501,850, and 5,961,960, patent application EP 0 669 323, U.S. Pat. Nos. 5,518,713, and 2,463,264, the article from *J. Am. Chem. Soc.*, 79, 5706–5708, 1957, the article published in *J. Am. Chem. Soc.*, 82, 609–611, 1960, patent application EP 0 921 126 and patent application EP 0 712 855.

As examples of preferred compounds of formula (VIII) of the 2-arylbenzazole family, mention may be made of 2-benzoxazol-2-yl-4-methylphenol, 2-(1H-benzimidazol-2-yl)-4-methoxyphenol or 2-benzothiazol-2-ylphenol, these compounds possibly being prepared, for example, according to the processes described in patent CH 350 763.

As examples of preferred compounds of formula (VIII) of the benzimidazolylbenzazole family, mention will be made of 2,2'-bis(benzimidazole), 5,5',6,6'-tetramethyl-2,2'-bis(benzimidazole), 5,5'-di-methyl-2,2'-bis(benzimidazole), 6-methoxy-2,2'-bis(benzimidazole), 2-(1H-benzimidazol-2-yl)benzothiazole, 2-(1H-benzimidazol-2-yl)benzoxazole and N,N'-dimethyl-2,2'-bis(benzimidazole), these compounds possibly being prepared according to the procedures described in patents U.S. Pat. Nos. 5,961,960 and 2,463,264.

As examples of preferred compounds of formula (VIII) of the phenylenebenzazole family, mention will be made of 1,4-phenylenebis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenebis(benzimidazolyl), 1,4-phenylenebis(N-2-ethylhexyl-2-benzimidazolyl) and 1,4-phenylenebis(N-trimethylsilylmethyl-2-benzimidazolyl), these compounds possibly being prepared according to the procedures described in patent U.S. Pat. No. 2,463,264 and in the publications *J. Am. Chem. Soc.*, 82, 609 (1960) and *J. Am. Chem. Soc.*, 79, 5706–5708 (1957).

As examples of preferred compounds of formula (VIII) of the benzofuranylbenzoxazole family, mention will be made of 2-(2-benzofuranyl)benzoxazole, 2-(benzofuranyl)-5-methylbenzoxazole and 2-(3-methyl-2-benzofuranyl) benzoxazole, these compounds possibly being prepared according to the procedures described in U.S. Pat. No. 5,518,713.

Preferred compounds of formula (IX) that may be mentioned, for example, include 2,6-diphenyl-1,7-dihydrobenzo[1,2-d;4,5-d']diimidazole, corresponding to the formula:

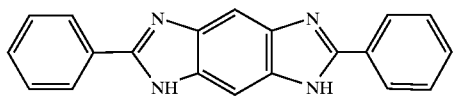

or 2,6-distyryl-1,7-dihydrobenzo[1,2-d;4,5-d']diimidazole or alternatively 2,6-di(p-tert-butylstyryl)-1,7-dihydro-benzo[1,2-d;4,5-d']diimidazole, which may be prepared according to the processes described in patent application EP 0 669 323.

A preferred compound of formula (X) that may be mentioned is 5,5'-bis[(2-phenyl)benzimidazole] of formula:

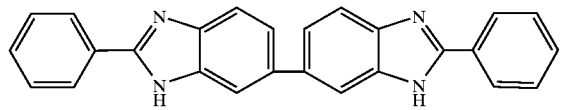

the preparation of which is described in *J. Chim. Phys.*, 64, 1602 (1967).

Among these insoluble organic compounds for screening out UV radiation, the ones most particularly preferred are 2-(1H-benzimidazol-2-yl)benzoxazole, 6-methoxy-2,2'-bis(benzimidazole), 2-(1H-benzimidazole-2-yl)benzothiazole, 1,4-phenylenebis(2-benzoxazolyl), 1,4-phenylenebis(2-benzimidazolyl), 1,3-phenylenebis-(2-benzoxazolyl), 1,2-phenylenebis(2-benzoxazolyl), 1,2-phenylenebis(2-benzimidazolyl) and 1,4-phenylene-bis(N-trimethylsilylmethyl-2-benzimidazolyl).

Another family of insoluble screening agents is that of the arylvinylene ketones chosen from those corresponding to one of the following formulae (XI) and (XII):

(XI)

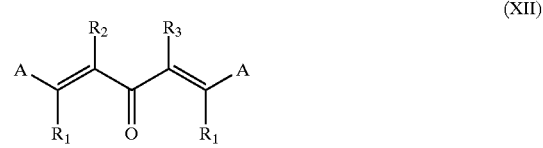

(XII)

in which:

n=1 or 2,

A, in formula (XI) when n=1 or in formula (XII), is an aryl radical chosen from formula (a) to (d) below, or in formula (XI) when n=2, is a radical chosen from formulae (e) to (h) below:

(a)

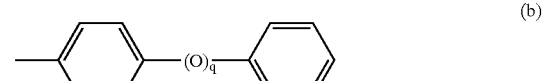

(b)

(c)

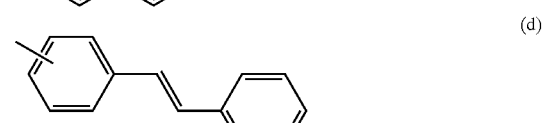

(d)

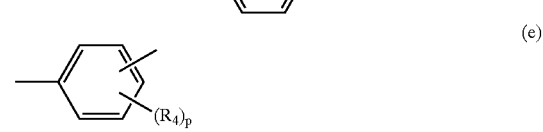

(e)

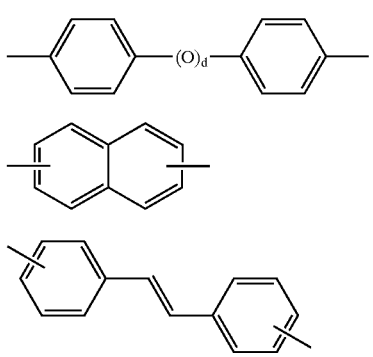

in which:
- each of the symbols $R_4$ independently represents an OH group, a halogen atom, a linear or branched $C_{1-6}$ alkyl group optionally containing a silicon atom, a linear or branched $C_{1-6}$ alkoxy group optionally containing a silicon atom, a linear or branched $C_{1-5}$ alkoxycarbonyl group, or a linear or branched $C_{1-6}$ alkylsulphonamide group optionally containing a silicon atom or an amino acid function,
- p represents an integer between 0 and 4 inclusive,
- q represents 0 or 1,
- $R_1$ represents hydrogen or an OH group,
- $R_2$ represents hydrogen, a linear or branched $C_{1-6}$ alkyl group optionally containing a silicon atom, a cyano group, a $C_{1-6}$ alkylsulphonyl group or a phenylsulphonyl group,
- $R_3$ represents a linear or branched $C_{1-6}$ alkyl group optionally containing a silicon atom or a phenyl group that can form a bicycle and optionally substituted with one or two radicals $R_4$,
- or $R_2$ and $R_3$ together form a monocyclic, bicyclic or tricyclic $C_{2-10}$ hydrocarbon-based residue, optionally interrupted with one or more nitrogen, sulphur and oxygen atoms and possibly containing another carbonyl, and optionally substituted with a linear or branched $C_1$–$C_8$ alkylsulphonamide group, optionally containing a silicon atom or an amino acid function; on condition that when n=1, $R_2$ and $R_3$ do not form a camphor nucleus.

As examples of insoluble compounds of formula (XI) in which n=1, for screening out UV radiation, mention may be made of the following families:

(1) Styryl ketone (Kao JP 04 134 042) such as 1-(3,4-dimethoxyphenyl)-4,4-dimethylpent-1-en-3-one:

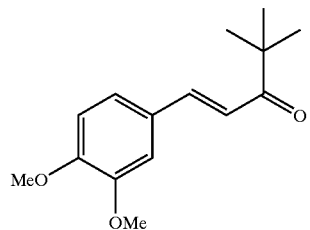

(2) Benzylidene cineole (E. Mariani et al., 16th IFSCC Congress, New York (1990)) such as 1,3,3-trimethyl-5-(4-methoxybenzylidene)-2-oxabicyclo[2.2.2]octan-6-one:

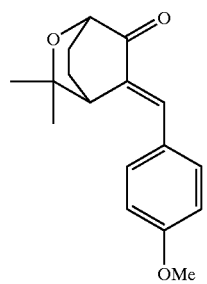

(3) Benzylidene chromanone (Kao JP 04 134 043) such as 3-(4-methoxybenzylidene)-2,3,4a,8a-tetrahydrochromen-4-one:

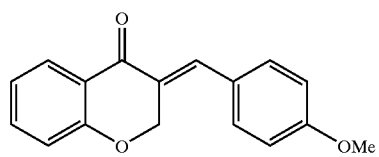

(4) Benzylidene thiochromanone (Kao JP 04 134 043) such as 3-(4-methoxybenzylidene)-2,3,4a,8a-tetrahydrochromen-4-thione:

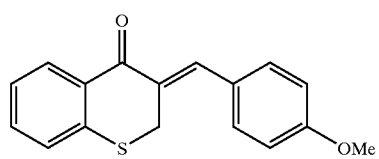

(5) Benzylidene quinuclidinone (Merck EP 0 576 974) such as 4-methoxybenzylidene-1-azabicyclo-[2.2.2]octan-3-one:

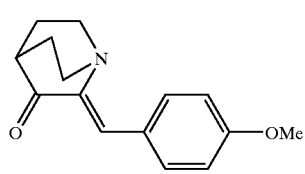

(6) Benzylidene cycloalkanone (Henkel FR 2 395 023) such as 2-(4-methoxybenzylidene)cyclopentanone and 2-(4-methoxybenzylidene)cyclohexanone:

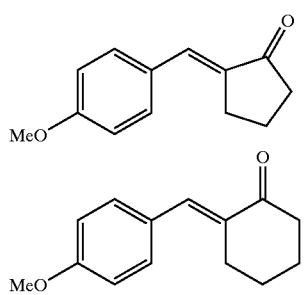

(7) Benzylidene hydantoin (Ajinomoto JP 01 158 090) such as 5-(3,4-dimethoxybenzylidene)imidazolidine-2,4-dione:

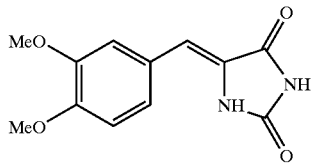

(8) Benzylidene indanone (Kao JP 04 134 043) such as 2-(4-methoxybenzylidene)indan-1-one:

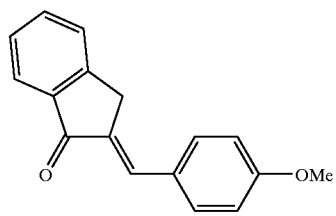

(9) Benzylidene tetralone (Kao JP 04 134 043) such as 2-(4-methoxybenzylidene)-3,4-dihydro-2H-naphthalen-1-one:

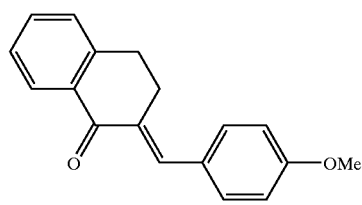

(10) Benzylidene furanone (L'Oreal EP 0 390 683) such as 4-(4-methoxybenzylidene)-2,2,5,5-tetramethyldihydrofuran-3-one:

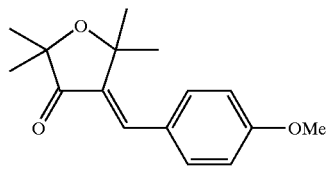

(11) Benzylidene benzofuranone (Kao JP 04 134 041) such as 2-benzylidenebenzofuran-3-one:

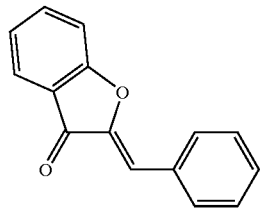

(12) Benzylidene indanedione such as 2-(3,5-di-tert-butyl-4-hydroxybenzylidene)indan-1,3-dione:

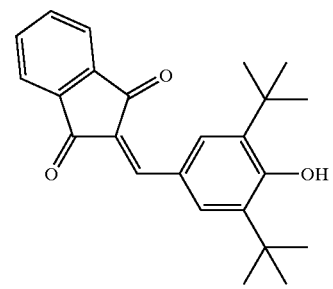

(13) Benzylidene benzothiofuranone (Kao JP 04 134 043) such as 2-benzylidenebenzo-[b]thiophen-3-one:

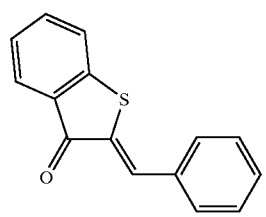

(14) Benzylidene barbituric such as 5-(4-methoxybenzylidene)-1,3-dimethylpyrimidine-2,4,6-trione:

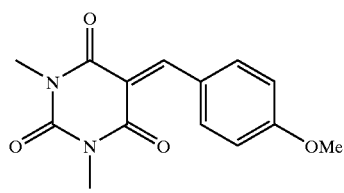

(15) Benzylidene pyrazolone such as 4-(4-methoxybenzylidene)-5-methyl-2-phenyl-2,4-dihydropyrazol-3-one:

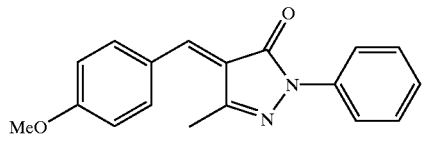

(16) Benzylidene imidazolone such as 5-(4-methoxybenzylidene)-2-phenyl-3,5-dihydroimidazol-4-one:

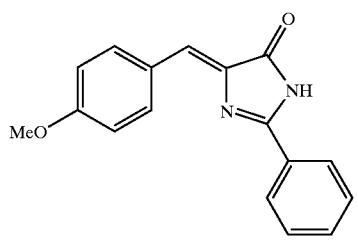

(17) Chalcone such as 1-(2-hydroxy-4-methoxyphenyl)-3-phenylpropenone:

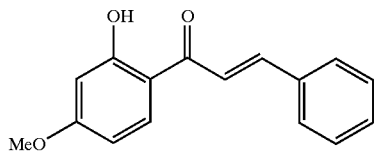

(18) Benzylidene one (screening tautomeric form of the dibenzoylmethanes; L'Oreal FR 2 506 156) such as 3-hydroxy-1-(2-hydroxy-4-methoxyphenyl)-3-phenylpropenone:

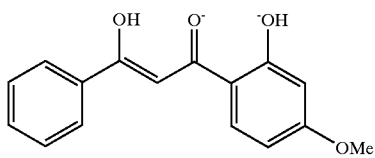

As examples of insoluble compounds of formula (XI) in which n=2, for screening out UV radiation, mention may be made of the following families:

(1) Phenylenebis(methylidene-nor-camphor) (Merck EP 0 693 471), such as 1,4-phenylenebis{3-methylidenebicyclo[2.2.1]heptan-2-one}:

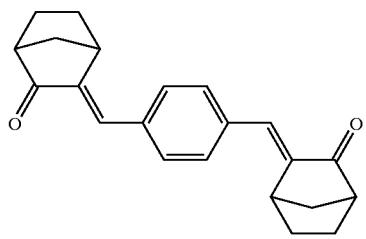

(2) Phenylenebis(methylidenecamphor) (L'Oreal FR 2 528 420) such as 1,4-phenylenebis{3-methylidene-1,7,7-trimethylbicyclo[2.2.1]-heptan-2-one}:

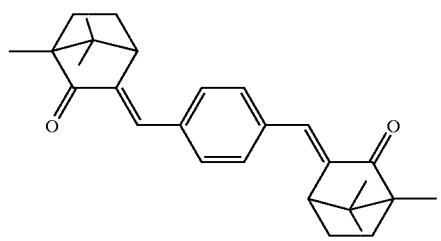

or 1,3-phenylenebis{3-methylidene-1,7,7-trimethylbicyclo[2.2.1]heptan-2-one}:

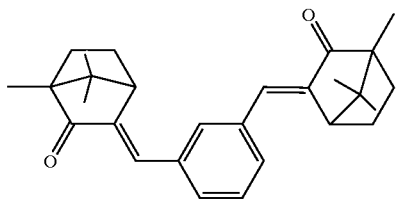

(3) Phenylenebis(methylidenecamphorsulphonamide) (L'Oreal FR 2 529 887) such as ethyl or 2-ethylhexyl 1,4-phenylenebis(3,3'-methylidenecamphor-10,10'-sulphonamide):

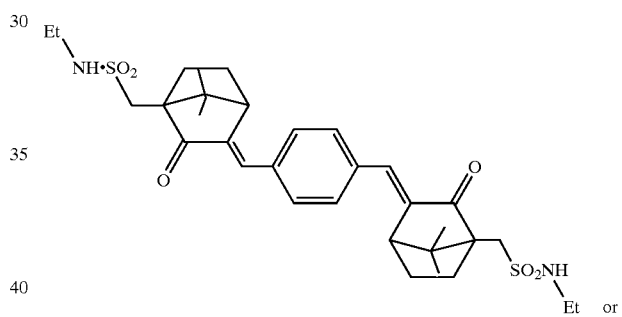

or

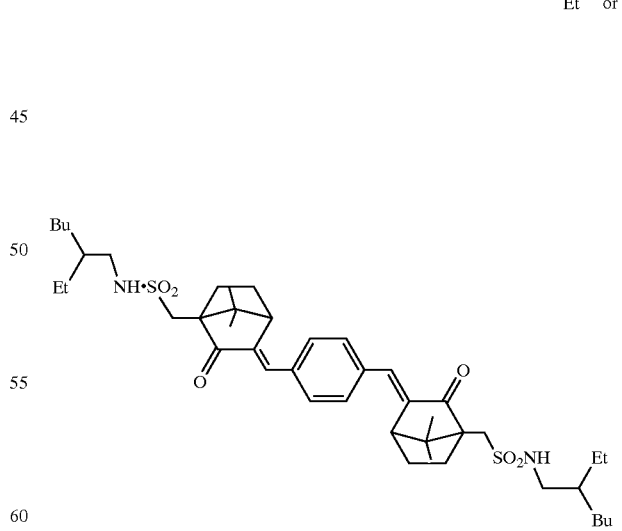

(4) Phenylenebis(methylidenecineole) (E. Mariani et al, 16th IFSCC Congress, New York (1990)) such as 1,4-phenylenebis{5-methylidene-3,3-dimethyl-2-oxabicyclo[2.2.2]octan-6-one}:

(5) Phenylenebis(methylidene ketotricyclodecane) (Merck EP 0 694 521) such as 1,4-phenylenebis(octahydro-4,7-methano-6-inden-5-one):

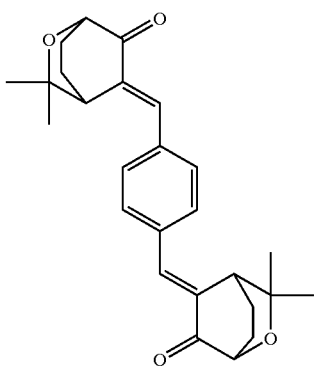

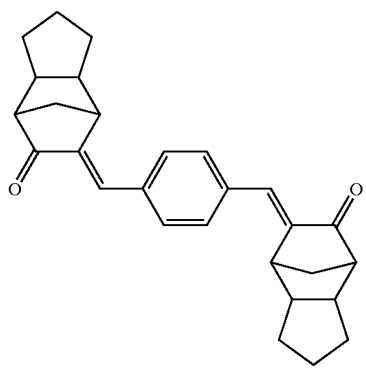

(6) Phenylenebis(alkylene ketone) (Kao JP 04 134 041) such as 1,4-phenylenebis(4,4-dimethylpent-1-en-3-one):

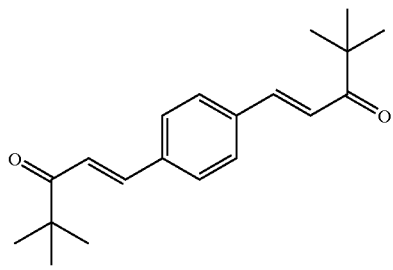

(7) Phenylenebis(methylidenefuranone) (L'Oreal FR 2 638 354) such as 1,4-phenylenebis(4-methylidene-2,2,5,5-tetramethyldihydrofuran-3-one):

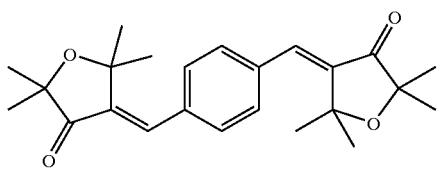

(8) Phenylenebis(methylidene quinuclidinone) (Merck EP 0 714 880) such as 1,4-phenylenebis{2-methylidene-1-azabicyclo[2.2.2]octan-3-one}:

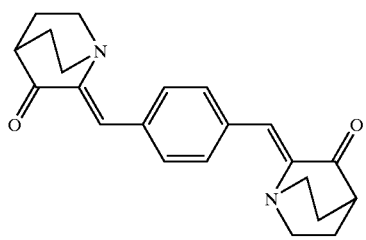

Examples of compounds of formula (XII) that may be mentioned include the following families:

(1) bis(benzylidene)cycloalkanone such as 2,5-dibenzylidenecyclopentanone:

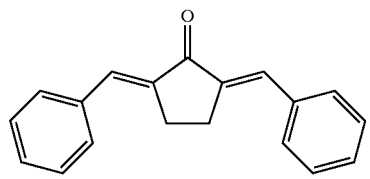

(2) gamma-pyrone (Kao JP 04 290 882) such as 2,6-bis(3,4-dimethoxyphenyl)pyran-4-one:

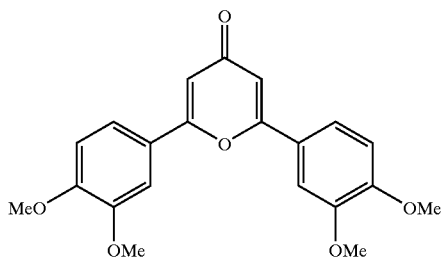

Another family of insoluble screening agents that may be used in the present invention are the acrylonitrile amide, sulphonamide and carbamate derivatives corresponding to the following formula:

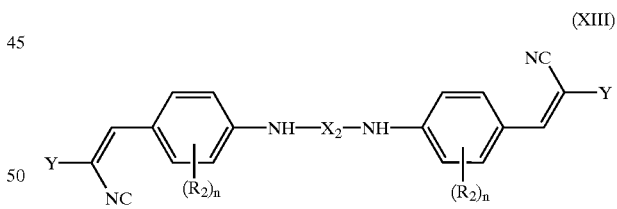

(XIII)

in which
$X_2$ represents a divalent radical of formula
—(C=O)—R'$_3$—(C=O)—,
—SO$_2$—R"$_3$—SO$_2$— or —(C=O)—O—R"$_3$—O—(C=O)—,
Y represents a radical —(C=O)—R$_4$ or —SO$_2$R$_5$,
R$_2$ represents a linear or branched C$_{1-8}$ alkyl group,
n is 0, 1 or 2,
R'$_3$ represents a single bond or R"$_3$,
R"$_3$ represents a linear or branched C$_{1-30}$ divalent alkylene radical or a linear or branched C$_{3-30}$ divalent alkenylene radical, which may bear one or more hydroxyl substituents and which may contain, in the carbon-based chain, one or more hetero atoms chosen from oxygen, nitrogen and silicon atoms, $R_4$ represents a radical —$OR_6$ or —$NHR_6$, $R_5$ represents a linear or branched $C_{1-30}$ alkyl radical or a phenyl nucleus that may be substituted with $C_{1-4}$ alkyl or alkoxy radicals, $R_6$ represents a linear or branched $C_{1-30}$ alkyl or $C_{3-30}$ alkenyl radical, which may bear one or more hydroxyl substituents and which may contain, in the carbon-based chain, one or more hetero atoms chosen from oxygen, nitrogen and silicon atoms.

Although, in formula (XIII) above, only the isomers in which the cyano substituent is in the cis position relative to the para-aminophenyl substituent are represented, this formula must be understood as also including the corresponding trans isomers for each of the two double bonds and, independently, the cyano and para-aminophenyl substituents may be in a cis or trans configuration relative to each other.

Another family of insoluble organic screening agents that may be used according to the present invention is formed by the phenylenebis(benzoxazinone) derivatives of formula:

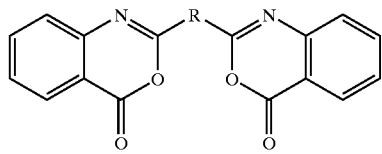

(XIV)

in which R represents a divalent aromatic residue chosen from the formulae (e) to (h) below:

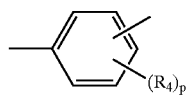

(e)

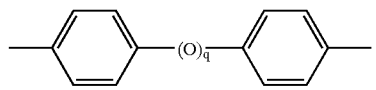

(f)

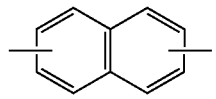

(g)

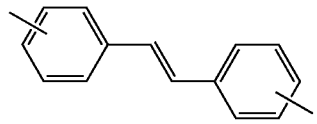

(h)

in which:

each of the symbols $R_4$ independently represents an OH group, a halogen atom, a linear or branched $C_{1-6}$ alkyl group optionally containing a silicon atom, a linear or branched $C_{1-6}$ alkoxy group optionally containing a silicon atom, a linear or branched $C_{1-5}$ alkoxycarbonyl group, or a linear or branched $C_{1-6}$ alkylsulphonamide group optionally containing a silicon atom or an amino acid function, p represents an integer between 0 and 4 inclusive, q represents 0 or 1.

Examples of insoluble compounds of formula (XIV) for screening out UV radiation that may be mentioned include the following derivatives:

2,2'-p-phenylenebis(3,1-benzoxazin-4-one), commercial product Cyasorb® UV-3638 from Cytec, 2,2'-(4,4'-biphenylene)bis(3,1-benzoxazin-4-one), 2,2'-(2,6-naphthylene)bis(3,1-benzoxazin-4-one).

Another particular family of insoluble organic screening agents is polyvalent metal salts (for example $Ca^{2+}$, $Zn^{2+}$, $Mg^{2+}$, $Ba^{2+}$, $Al^{3+}$ or $Zr^{4+}$) of sulphonated or carboxylated organic screening agents, such as polyvalent metal salts of sulphonated benzylidenecamphor derivatives such as those described in patent application FR-A-2 639 347, polyvalent metal salts of sulphonated benzimidazole derivatives such as those described in patent application EP-A-893 119, and polyvalent metal salts of cinnamic acid derivatives such as those described in patent application JP-87 166 517.

Mention may also be made of complexes of metals or of ammonium or of substituted ammonium of UV-A and/or UV-B organic screening agents such as those described in patent applications WO 93/10753, WO 93/11095 and WO 95/05150.

The dispersions of insoluble organic UV screening agents that it is proposed to stabilize using the amphiphilic copolymers described above are preferably aqueous dispersions, i.e. water constitutes all or most of the liquid dispersion medium.

They preferably contain from 5% to 70% by weight and in particular from 30% to 50% by weight of particles of insoluble organic compound comprising at least one group that absorbs UV radiation.

As mentioned above, the mean particle size of the insoluble organic compound comprising at least one group that absorbs UV radiation is between 10 nm and 5 μm.

The mean particle size of the insoluble organic compound comprising at least one group that absorbs UV radiation is preferably between 10 nm and 2 μm, in particular between 20 nm and 1.5 μm and ideally between 30 nm and 1.0 μm.

In general, the mean particle size will correspond to the number-average diameter distribution.

The mean particle size may be determined by any standard method such as optical methods (quasielastic scattering or laser scattering), centrifugation methods or methods of microscopic visualization and image analysis.

The amount of amphiphilic copolymer required to obtain satisfactory stability and persistence properties depends, inter alia, on the nature of the amphiphilic copolymer and on the nature, concentration, size and specific surface area of the particles of the insoluble organic UV screening agents to be stabilized.

It has been found that it is possible to satisfactorily stabilize the dispersions of insoluble organic UV screening agents of the present invention by using an amount of amphiphilic copolymer comprising at least one hydrophilic block and at least one hydrophobic block of between 1 and 10 mg/m² and preferably between 1 and 5 mg/m², of surface area of particles of insoluble organic compound comprising at least one group that absorbs UV radiation.

A subject of the present invention is also a process for preparing dispersions of insoluble organic compounds comprising at least one group that absorbs UV radiation. This process consists in subjecting particles of the said organic compound, suspended in a liquid medium, to a step of particle size reduction until a mean size of between 10 nm and 5 μm is obtained, and in adding, before, during or after the step of size reduction, at least one amphiphilic copolymer comprising at least one hydrophilic block and at least one hydrophobic block such as those described above.

The step of particle size reduction in the process for manufacturing dispersions of the present invention may be carried out by any suitable means, such as dry grinding or grinding in a solvent medium, screening, atomization, micronization, spraying or any chemical process such as precipitation by emulsion or dilution.

According to one preferred embodiment of the process of the present invention, the step of particle size reduction is a grinding operation in an aqueous medium.

Although it is possible to add the amphiphilic copolymer alone after the grinding step, one preferred embodiment comprises the addition of the amphiphilic copolymer before grinding in the premix, i.e. in the suspension of coarse particles in a liquid medium, or alternatively during the grinding step.

One example of a process for reducing the size of the particles by grinding insoluble organic screening agents is described in documents WO 95/22959 and WO 97/03643.

The grinding apparatus used according to these documents may be a jet mill, a ball mill, a vibration mill or a hammer mill and preferably a high-spin-speed mill or an impact mill and more particularly a rotary ball mill, a vibrating mill, a tube mill or a rod mill.

A subject of the invention is also dispersions of particles of insoluble organic compounds comprising at least one group that absorbs UV radiation, prepared according to the process described above, containing a dispersant chosen from a particular group of amphiphilic copolymers comprising at least one hydrophilic block and at least one hydrophobic block, and also cosmetic compositions for topical application, in particular compositions intended for photoprotecting the skin and/or the hair, prepared by dilution of its dispersions in a cosmetically acceptable medium.

The particular group of amphiphilic copolymers includes:

(1) polyalkoxylated aliphatic alcohols of formula:

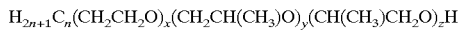

$H_{2n+1}C_n(CH_2CH_2O)_x(CH_2CH(CH_3)O)_y(CH(CH_3)CH_2O)_zH$ in which
n is an integer between 5 and 20 and preferably between 7 and 19,
x is an integer between 2 and 20 and preferably between 4 and 10,
y is an integer between 2 and 20 and preferably between 4 and 10,
the sum of y+z being an integer between 2 and 20 and preferably between 2 and 20.

(2) triblock copolymers of ethylene oxide and of propylene oxide, of formula

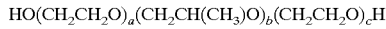

$HO(CH_2CH_2O)_a(CH_2CH(CH_3)O)_b(CH_2CH_2O)_cH$ in which a represents an integer between 2 and 150, b represents an integer between 10 and 80 and c represents an integer between 2 and 150;

(3) the products of condensation of block copolymers of ethylene oxide and of propylene oxide with ethylenediamine, corresponding to the formula:

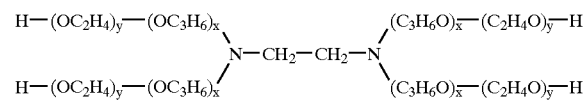

(4) block copolymers of styrene and of ethylene oxide,
(5) polyalkoxylated polyolefin succinates, and in particular the polyethoxylated polyisobutylene succinate of formula:

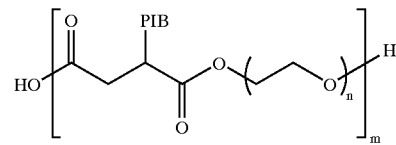

in which
PIB represents a polyisobutylene chain, n represents an integer between 2 and 15 and preferably between 7 and 10, and m represents an integer between 2 and 15, preferably between 2 and 6;

(6) block terpolymers of (meth)acrylic acid, of a $C_{10-30}$ alkyl (meth)acrylate and of polyethylene glycol (meth)acrylate.

The insoluble organic compounds comprising at least one group that absorbs UV radiation, the mean particle size of these screening agents and also the amount of amphiphilic copolymer used to stabilize them are the same as those specified above.

The cosmetic compositions of the present invention, obtained by dilution in a cosmetically acceptable medium, preferably contain from 0.1% to 15% by weight and in particular from 0.2% to 10% by weight of particles of insoluble organic compound comprising at least one group that absorbs UV radiation.

The cosmetic compositions of the present invention may also contain one or more water-soluble or liposoluble organic sunscreens that are active in the UV-A and/or UV-B range.

These water-soluble or liposoluble sunscreens may be chosen especially from cinnamic derivatives, dibenzoylmethane derivatives, salicylic derivatives, benzylidenecamphor derivatives, soluble triazine derivatives such as those described in patents or patent applications U.S. Pat. No. 4,367,390, EP 0 863 145, EP 0 517 104, EP 0 570 838, EP 0 796 851, EP 0 775 698, EP 0 878 469, EP 0 933 376, EP 0 507 691, EP 0 507 692, EP 0 790 243, EP 0 944 624 and U.S. Pat. No. 4,724,137; benzophenone derivatives; β,β'-diphenyl acrylate derivatives; phenylbenzimidazole derivatives; anthranilic derivatives; imidazoline derivatives; p-aminobenzoic acid derivatives; screening hydrocarbon-based polymers and screening silicones such as those described especially in patent application WO 93/04665; dimers derived from α-alkylstyrene as described in patent application DE 198 55 649; and also mixtures of these screening agents.

As examples of such additional water-soluble or liposoluble sunscreens that are active in the UV-A and/or UV-B range, mention may be made of the following compounds, denoted by their INCI name, and also mixtures thereof:

para-Aminobenzoic Acid Derivatives:
(a) PABA,
(b) Ethyl PABA,
(c) Ethyl dihydroxypropyl PABA,
(d) Ethylhexyl dimethyl PABA sold in particular under the trade name "Escalol 507" by ISP,
(e) Glyceryl PABA,
(d) PEG-25 PABA sold under the trade name "Uvinul P25" by BASF, Salicylic Derivatives:
(a) Homosalate sold under the trade name "Eusolex HMS" by Rona/EM Industries,
(b) Ethylhexyl salicylate sold under the trade name "Neo Heliopan OS" by Haarmann and Reimer, (c) Dipropylene glycol salicylate sold under the trade name "Dipsal" by Scher,
(d) TEA salicylate sold under the trade name "Neo Heliopan TS" by Haarmann and Reimer, Dibenzoylmethane Derivatives:
(a) Butyl methoxydibenzoylmethane sold in particular under the trade name "Parsol 1789" by Hoffmann LaRoche,
(b) Isopropyldibenzoylmethane, Cinnamic Derivatives:
(a) Ethylhexyl methoxycinnamate sold in particular under the trade name "Parsol MCX" by Hoffmann LaRoche,
(b) Isopropyl methoxycinnamate,
(c) Isoamyl methoxycinnamate sold under the trade name "Neo Heliopan E 1000" by Haarmann and Reimer,
(d) Cinoxate,
(e) DEA methoxycinnamate,
(f) Diisopropyl methylcinnamate,
(g) Glyceryl ethylhexanoate dimethoxycinnamate, β,β'-diphenylacrylate Derivatives:
(a) Octocrylene sold in particular under the trade name "Uvinul-539" by BASF, Benzophenone Derivatives:
(a) Benzophenone-1 sold under the trade name "Uvinul 400" by BASF,
(b) Benzophenone-2 sold under the trade name "Uvinul D50" by BASF,
(c) Benzophenone-3 or Oxybenzone, sold under the trade name "Uvinul M-40" by BASF,
(d) Benzophenone-4 sold under the trade name "Uvinul MS-40" by BASF,
(e) Benzophenone-5,
(f) Benzophenone-6 sold under the trade name "Helisorb 11" by Norquay,
(g) Benzophenone-8 sold under the trade name "Spectra-Sorb UV-24" by American Cyanamid,
(h) Benzophenone-9 sold under the trade name "Uvinul DS-49" by BASF,
(i) Benzophenone-12, Benzylidenecamphor Derivatives:
(a) Benzylidenecamphorsulphonic acid manufactured under the name "Mexoryl SL" by Chimex,
(b) Camphor benzalkonium methosulphate manufactured under the name "Mexoryl SO" by Chimex,
(c) Terephthalylidenedicamphorsulphonic acid manufactured under the name "Mexoryl SX" by Chimex,
(d) Polyacrylamidomethylbenzylidenecamphor manufactured under the name "Mexoryl SW" by Chimex, Phenylbenzimidazole Derivatives:
(a) Phenylbenzimidazolesulphonic acid sold in particular under the trade name "Eusolex 232" by Merck,
(b) Benzimidazilate sold under the trade name "Neo Heliopan AP" by Haarmann and Reimer, Triazine Derivatives:
(a) Anisotriazine sold under the trade name "Tinosorb S" by Ciba-Geigy,
(b) Ethylhexyltriazone sold in particular under the trade name "Uvinul T150" by BASF,
(c) Diethylhexylbutamidotriazone sold under the trade name "Uvasorb HEB" by Sigma 3V, Phenylbenzotriazole Derivatives:
(a) Drometrizole trisiloxane sold under the trade name "Silatrizole" by Rhodia Chimie, Anthranilic Derivatives:
(a) Menthyl anthranilate sold under the trade name "Neo Heliopan MA" by Haarmann and Reimer, Imidazoline Derivatives:
(a) Ethylhexyldimethoxybenzylidenedioxoimidazoline propionate, Benzalmalonate Derivatives:
(a) Polyorganosiloxane containing benzalmalonate functions, sold under the trade name "Parsol SLX" by Hoffmann LaRoche.

The water-soluble or liposoluble organic UV screening agents that are more particularly preferred are chosen from the following compounds:

Ethylhexyl salicylate,
Butyl methoxydibenzoylmethane,
Ethylhexyl methoxycinnamate,
Octocrylene,
Phenylbenzimidazolesulphonic acid,
Terephthalylidenedicamphorsulphonic acid,
Benzophenone-3,
Benzophenone-4,
Benzophenone-5,
Benzimidazilate,
Anisotriazine,
Ethylhexyltriazone,
Diethylhexylbutamidotriazone,
Drometrizole trisiloxane, and mixtures thereof.

The cosmetic compositions according to the invention may also contain agents for artificially tanning and/or browning the skin (self-tanning agents) such as dihydroxyacetone (DHA).

The cosmetic compositions according to the invention may also contain one or more mineral pigments and in particular metal oxide nanopigments, that may be coated or uncoated, such as, for example, nanopigments of titanium oxide in amorphous or crystalline (rutile and/or anatase) form, of iron oxide, of zinc oxide, of zirconium oxide or of cerium oxide. These nanopigments have a mean particle size of between 5 nm and 100 nm and preferably between 10 nm and 50 nm, and are all known UV-photoprotective agents.

These nanopigments may be coated with known coating agents such as, for example, alumina and/or aluminium stearate.

Such coated or uncoated nanopigments are described, for example, in patent applications EP-A-0 518 772 and EP-A-0 518 773.

The cosmetic compositions may also contain common formulation adjuvants such as fatty substances, physiologically acceptable organic solvents, silicones, surfactants, anionic, cationic, nonionic or amphoteric polymers or mixtures thereof, thickeners, antioxidants, opacifiers, stabilizers, antifoams, fragrances, preserving agents, fillers, sequestering agents, propellants, pH modifiers and colorants, and mixtures thereof.

They may also contain one or more cosmetic active principles chosen, for example, from softeners, hydroxy acids, vitamins, moisturizers, emollients, free-radical scavengers, substance P antagonists and anti-inflammatory agents, and mixtures of these compounds.

The fatty substances may consist of an oil or a wax or mixtures thereof, and they also comprise fatty acids, fatty alcohols and fatty acid esters. The oils may be chosen from animal, plant, mineral and synthetic oils and especially from liquid petroleum jelly, liquid paraffin, silicone oils, that may be volatile or non-volatile, isoparaffins, polyolefins, fluoro oils and perfluoro oils. Similarly, the waxes may be chosen from animal, fossil, plant, mineral and synthetic waxes that are known per se.

Among the organic solvents that may be mentioned are lower alcohols and polyols such as ethanol, isopropanol, propylene glycol, glycerol and sorbitol.

The thickeners may be chosen especially from guar gums and celluloses, that may be modified or unmodified, such as hydroxypropyl guar gum, methylhydroxyethylcellulose, hydroxypropylmethylcellulose or hydroxyethylcellulose.

Needless to say, the person skilled in the art will take care to select this or these optional additional compound(s) and/or the amounts thereof such that the advantageous properties intrinsic to the invention, and in particular the stability of the dispersions, are not adversely affected by the envisaged addition(s).

The compositions of the invention may be prepared according to techniques that are well known to those skilled in the art, in particular those intended for preparing emulsions of oil-in-water or water-in-oil type.

This composition may be in particular in the form of a simple or complex emulsion (O/W, W/O, O/W/O or W/O/W emulsion) such as a cream, a milk, a gel or a cream-gel, and may optionally be packaged as an aerosol and be in the form of a mousse or a spray.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The cosmetic composition of the invention may be used as a composition for protecting the human epidermis or the hair against ultraviolet rays, as an antisun composition or as a makeup product.

When the cosmetic composition according to the invention is used for protecting the human epidermis against UV rays, or as an antisun composition, it may be in the form of a suspension or a dispersion in solvents or fatty substances, in the form of a nonionic vesicular dispersion or in the form of an emulsion, preferably of oil-in-water type, such as a cream or a milk, or in the form of an ointment, a gel, a cream-gel, an aerosol mousse or a spray.

When the cosmetic composition according to the invention is used for protecting the hair against UV rays, it may be in the form of a shampoo, a lotion, a gel, an emulsion or a nonionic vesicular dispersion and may constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a composition for permanent-waving, straightening, dyeing or bleaching the hair.

When the composition is used as a makeup product for the eyelashes, the eyebrows or the skin, such as an epidermal treatment cream, a foundation, a tube of lipstick, an eyeshadow, a face powder, a mascara or an eyeliner, it may be in aqueous form, for instance oil-in-water or water-in-oil emulsions, nonionic vesicular dispersions or suspensions.

As a guide, for the antisun formulations in accordance with the invention, which contain a support of oil-in-water emulsion type, the aqueous phase generally represents from 50% to 95% by weight and preferably from 70% to 90% by weight, relative to the total formulation, the oily phase represents from 5% to 50% by weight and preferably from 10% to 30% by weight, relative to the total formulation, and the (co)emulsifier(s) represent(s) from 0.5% to 20% by weight and preferably from 2% to 10% by weight, relative to the total formulation.

What is claimed is:

1. A process for stabilizing a dispersion of an insoluble organic compound comprising at least one group that absorbs UV radiation, and which is in the form of particles with a mean size of between 10 nm and 5 μm, comprising adding to the dispersion at least one amphiphilic copolymer comprising at least one hydrophilic block and at least one hydrophobic block, the amphiphilic copolymer being a nonionic polymer which is:

(1) a polyalkoxylated aliphatic alcohol of the formula:

$$H_{2n+1}C_n(CH_2CH_2O)_x(CH_2CH(CH_3)O)_y(CH(CH_3)CH_2O)_zH$$

in which
   n is an integer between 5 and 20,
   x is an integer between 2 and 20,
   y is an integer between 2 and 20,
   the sum of y+z being an integer between 2 and 20;

(2) a triblock copolymer of ethylene oxide and of propylene oxide of the formula:

$$HO(CH_2CH_2O)_a(CH_2CH(CH_3)O)_b(CH_2CH_2O)_cH$$

in which a represents an integer between 2 and 150, b represents an integer between 10 and 80 and c represents an integer between 2 and 150;

(3) a product of condensation of a block copolymer of ethylene oxide and propylene oxide with ethylenediamine of the formula:

$$\begin{array}{c}H-(OC_2H_4)_y-(OC_3H_6)_x\\ \phantom{H-(OC_2H_4)_y-(OC_3H_6)_x}\diagdown\\ \phantom{xxxxxxxxx}N-CH_2-CH_2-N\\ \phantom{H-(OC_2H_4)_y-(OC_3H_6)_x}\diagup\\ H-(OC_2H_4)_y-(OC_3H_6)_x\end{array}\begin{array}{c}(C_3H_6O)_{\bar{x}}-(C_2H_4O)_{\bar{y}}-H\\ \\ \\ \\ (C_3H_6O)_{\bar{x}}-(C_2H_4O)_{\bar{y}}-H\end{array}$$

(4) a block copolymer of styrene and ethylene oxide:

(5) a polyethoxylated polyolefin succinate which is a polyethoxylated polyisobutylene succinate of the formula:

$$HO-\left[\underset{O}{\underset{\|}{C}}-CH_2-\underset{PIB}{\underset{|}{CH}}-\underset{O}{\underset{\|}{C}}-O-(CH_2CH_2O)_n\right]_m-H$$

in which
   PIB represents a polyisobutylene chain, n represents an integer between 2 and 15, and m represents an integer between 2 and 15; or (6) a block terpolymer of (meth)acrylic acid, a $C_{10-30}$ alkyl (meth)acrylate and polyethylene glycol (meth)acrylate.

2. The process of claim 1, wherein the dispersion of the insoluble organic compound is an aqueous dispersion.

3. The process of claim 1, wherein the insoluble organic compound is an insoluble UV screening agent which is oxalanilide, triazine, benzotriazole, vinylamide, cinnamide, benzazole, benzofuran, arylvinylidene ketone, acrylonitrile amide, acrylonitrile sulphonamide, acrylonitrile carbamate or phenylenebis(benzoxazinone).

4. The process of claim 3, wherein the benzotriazole has the formula:

(III)

in which $R_5$ denotes a hydrogen atom or a $C_{1-18}$ alkyl radical, $R_6$ and $R_7$, which may be identical or different, denote a $C_{1-18}$ alkyl radical optionally substituted with a phenyl group, or has the formula:

(IV)

in which $R_8$ and $R_9$, which may be identical or different, each represent a $C_{1-18}$ alkyl radical optionally substituted with one or more radicals which are $C_{1-4}$ alkyl, $C_{5-12}$ cycloalkyl or aryl.

5. The process of claim 1, wherein the mean particle size of the insoluble organic compound is between 10 nm and 2 μm.

6. The process of claim 1, wherein the dispersion contains from 5% to 70% by weight of particles of insoluble organic compound.

7. The process of claim 1, wherein the amphiphilic copolymer is used in a proportion of from 1 to 10 mg/m² of surface area of particles of insoluble organic compound.

8. A process for preparing a dispersion of an insoluble organic compound comprising at least one group that absorbs UV radiation, comprising subjecting particles of the organic compound, suspended in a liquid medium, to a step of particle size reduction until a mean particle size of between 10 nm and 5 μm is obtained, and adding, before, during or after the step of particle size reduction, at least one amphiphilic copolymer comprising at least one hydrophilic block and at least one hydrophobic block, the amphiphilic copolymer being a nonionic polymer which is:

(1) a polyalkoxylated aliphatic alcohol of the formula:

$$H_{2n+1}C_n(CH_2CH_2O)_x(CH_2CH(CH_3)O)_y(CH(CH_3)CH_2O)_zH$$

in which n is an integer between 5 and 20, x is an integer between 2 and 20, y is an integer between 2 and 20, the sum of y+z being an integer between 2 and 20;

(2) a triblock copolymer of ethylene oxide and of propylene oxide of the formula:

$$HO(CH_2CH_2O)_a(CH_2CH(CH_3)O)_b(CH_2CH_2O)_cH$$

in which a represents an integer between 2 and 150, b represents an integer between 10 and 80 and c represents an integer between 2 and 150;

(3) a product of condensation of a block copolymer of ethylene oxide and propylene oxide with ethylenediamine of the formula:

(4) a block copolymer of styrene and ethylene oxide;

(5) a polyethoxylated polyolefin succinate which is a polyethoxylated polyisobutylene succinate of the formula:

in which

PIB represents a polyisobutylene chain, n represents an integer between 2 and 15, and m represents an integer between 2 and 15; or (6) a block terpolymer of (meth)acrylic acid, a $C_{10-30}$ alkyl (meth)acrylate and polyethylene glycol (meth)acrylate.

9. The process of claim 8, wherein the step of particle size reduction comprises a grinding operation in an aqueous medium.

10. The process of claim 9, wherein the amphiphilic copolymer is added before or during the grinding step.

11. The process of claim 8, wherein the amphiphilic copolymer is a nonionic polymer.

12. The process of claim 8, wherein the insoluble organic compound is an insoluble UV screening agent which is oxalanilide, triazine, benzotriazole, vinylamide, cinnamide, benzazole, benzofuran, arylvinylidene ketone, acrylonitrile amide, acrylonitrile sulphonamide, acrylonitrile carbamate or phenylenebis(benzoxazinone).

13. The process of claim 12, wherein the benzotriazole has the formula:

(III)

in which $R_5$ denotes a hydrogen atom or a $C_{1-18}$ alkyl radical, $R_6$ and $R_7$, which may be identical or different, denote a $C_{1-18}$ alkyl radical optionally substituted with a phenyl group, or has the formula:

(IV)

[Structure: bis-benzotriazole phenol methylene compound with R8 and R9 substituents]

in which R$_8$ and R$_9$, which may be identical or different, each represent a C$_{1-18}$ is alkyl radical optionally substituted with one or more radicals which are C$_{1-14}$ alkyl, C$_{5-12}$ cycloalkyl or aryl.

14. A dispersion comprising, in a liquid medium,
(a) at least one insoluble organic compound comprising at least one group that screens out UV radiation, in the form of particles with a mean size of between 10 nm and 5 μm, and
(b) as dispersant, at least one amphiphilic copolymer comprising at least one hydrophilic block and at least one hydrophobic block, wherein the dispersant is:
(1) a polyalkoxylated aliphatic alcohol of formula:

$$H_{2n+1}C_n(CH_2CH_2O)_x(CH_2CH(CH_3)O)_y(CH(CH_3)CH_2O)_zH$$

in which
n is an integer between 5 and 20,
x is an integer between 2 and 20,
y is an integer between 2 and 20,
the sum of y+z being an integer between 2 and 20;
(2) a triblock copolymer of ethylene oxide and propylene oxide of formula:

$$HO(CH_2CH_2O)_a(CH_2CH(CH_3)O)_b(CH_2CH_2O)_cH$$

in which a represents an integer between 2 and 150, b represents an integer between 10 and 80 and c represents an integer between 2 and 150;
(3) a product of condensation of a block copolymer of ethylene oxide and propylene oxide with ethylenediamine corresponding to the formula:

$$\begin{array}{c} H-(OC_2H_4)_y-(OC_3H_6)_x \\ H-(OC_2H_4)_y-(OC_3H_6)_x \end{array} N-CH_2-CH_2-N \begin{array}{c} (C_3H_6O)_x-(C_2H_4O)_y-H \\ (C_3H_6O)_x-(C_2H_4O)_y-H \end{array}$$

(4) a block copolymer of styrene and ethylene oxide;
(5) a polyethoxylated polyolefin succinate which is a polyethoxylated polyisobutylene succinate of formula:

[Structure: polyisobutylene succinate ethoxylate with PIB group, showing HO-, C=O, O-(C2H4O)n-H repeating units, m subscript]

in which
PIB represents a polyisobutylene chain, n represents an integer between 2 and 15, and m represents an integer between 2 and 15; or (6) a block terpolymer of (meth)acrylic acid, C$_{10-30}$ alkyl (meth)acrylate and polyethylene glycol (meth)acrylate.
15. The dispersion of claim 14, wherein the dispersion contains from 5% to 70% by weight of particles of insoluble organic compound.
16. The dispersion of claim 14, wherein the dispersion contains as dispersant from 1 to 10 mg of amphiphilic copolymer per m$^2$ of surface area of particles of insoluble organic compound.
17. The dispersion of claim 14, wherein the liquid medium is an aqueous medium.
18. The dispersion of claim 14, wherein the amphiphilic copolymer is a nonionic polymer.
19. The dispersion of claim 14, wherein the insoluble organic compound is an insoluble UV screening agent which is oxalanilide, triazine, benzotriazole, vinylamide, cinnamide, benzazole, benzofuran, arylvinylidene ketone, acrylonitrile amide, acrylonitrile sulphonamide, acrylonitrile carbamate or phenylenebis(benzoxazinone).
20. The dispersion of claim 19, wherein the benzotriazole has the formula:

(III)

[Structure: benzotriazole phenol with R5, R6, R7 substituents]

in which R$_5$ denotes a hydrogen atom or a C$_{1-18}$ alkyl radical, R$_6$ and R$_7$, which may be identical or different, denote a C$_{1-18}$ alkyl radical optionally substituted with a phenyl group, or has the formula:

(IV)

[Structure: bis-benzotriazole phenol methylene compound with R8 and R9 substituents]

in which R$_8$ and R$_9$, which may be identical or different, each represent a C$_{1-18}$ alkyl radical optionally substituted with one or more radicals which are C$_{1-4}$ alkyl, C$_{5-12}$ cycloalkyl or aryl.
21. The dispersion of claim 14, wherein the mean particle size of the insoluble organic compound is between 10 nm and 2 μm.
22. A cosmetic composition for topical use, comprising in a cosmetically acceptable medium,
(a) at least one insoluble organic compound comprising at least one group that screens out UV radiation, in the form of particles with a mean size of between 10 nm and 5 μm, and
(b) at least one dispersant chosen from amphiphilic copolymers comprising at least one hydrophilic block and at least one hydrophobic block, prepared by dilution of a dispersion according to claim 14, in a cosmetically acceptable medium.

23. The composition of claim 22, which contains from 0.1% to 15% by weight of particles of the insoluble organic compound.

24. The composition of claim 22, which also contains one or more water-soluble or liposoluble organic sunscreens that are active in the UV-A and/or UV-B range.

25. The cosmetic composition of claim 24, wherein the soluble organic sunscreens are ethylhexyl salicylate, butyl methoxydibenzoylmethane, ethylhexyl methoxycinnamate, octocrylene, phenylbenzimidazole sulphonic acid, terephthalylidene dicamphor sulphonic acid, benzophenone-3, benzophenone-4, benzophenone-5, 4-methylbenzylidenecamphor, benzimidazilate, anisotriazine, ethylhexyl triazone, diethylhexyl butamido triazone, methylene bis-benzotriazolyl tetramethylbutylphenol, drometrizole trisiloxane, or mixtures thereof.

26. The cosmetic composition of claim 22, which further contains one or more mineral pigments.

27. The cosmetic composition of claim 26, wherein the mineral pigments are nanopigments of metal oxides, which are optionally coated, or mixtures thereof.

28. The cosmetic composition of claim 27, wherein the metal oxides are titanium oxide, iron oxide, zinc oxide, zirconium oxide or cerium oxide.

29. The cosmetic composition of claim 27, wherein the nanopigments have a mean particle size of between 5 nm and 100 nm.

30. The cosmetic composition of claim 22, which also contains at least one agent for artificially tanning and/or browning the skin.

31. The cosmetic composition of claim 22, which also contains one or more formulation adjuvants which are a fatty substance, a physiologically acceptable organic solvent, a thickener, an antioxidant, an opacifier, a stabilizer, an antifoam, a fragrance, a preserving agent, a filler, a sequestering agent, a propellant, a pH modifier and a colorant, or mixtures thereof.

32. The cosmetic composition of claim 22, which also contains one or more cosmetic active principles which are a vitamin, a softener, a hydroxy acid, a moisturizer, an emollient, a free-radical scavenger, a substance P antagonist, an anti-inflammatory agent, or mixtures thereof.

33. The cosmetic composition of claim 22, which is a cosmetic composition for protecting the skin or the hair, an antisun composition or a makeup product.

* * * * *